US010980587B2

United States Patent
Nolan et al.

(10) Patent No.: US 10,980,587 B2
(45) Date of Patent: Apr. 20, 2021

(54) ADAPTOR FOR USE WITH A DRIVER, A DRILL, AND A CANNULA FOR DRILLING INTO BONE

(71) Applicant: Medtronic Holding Company Sàrl, Tolochenaz (CH)

(72) Inventors: Travis J. Nolan, Carmel, CA (US); Calin Druma, San Jose, CA (US); Neil S. Sasaki, San Jose, CA (US)

(73) Assignee: MEDTRONIC HOLDING COMPANY SÀRL, Tolochenaz (CH)

( * ) Notice: Subject to any disclaimer, the term of this patent is extended or adjusted under 35 U.S.C. 154(b) by 583 days.

(21) Appl. No.: 15/880,088

(22) Filed: Jan. 25, 2018

(65) Prior Publication Data

US 2019/0223930 A1     Jul. 25, 2019

(51) Int. Cl.
*A61B 17/88*      (2006.01)
*A61B 17/16*      (2006.01)
(Continued)

(52) U.S. Cl.
CPC ...... *A61B 17/8811* (2013.01); *A61B 17/1615* (2013.01); *A61B 17/1622* (2013.01);
(Continued)

(58) Field of Classification Search
CPC ... A61B 17/162; A61B 17/1757; A61B 17/24; A61B 17/32; A61B 17/1615; A61B 17/3472; A61B 17/3476; A61B 2017/0046; A61B 2017/00477; A61B 10/025; A61B 17/8811; A61B 17/1622; A61B 17/1628; A61B 17/1633; A61B 17/1671; A61B 17/8819; A61M 2005/1585; A61M 5/158
(Continued)

(56) References Cited

U.S. PATENT DOCUMENTS 4,265,231 A    5/1981   Scheller, Jr. et al.
4,549,538 A    10/1985   Schadrack et al.
(Continued)

FOREIGN PATENT DOCUMENTS

CN       2340380 Y    9/1999
DE   202016107414 U1    2/2017
(Continued)

OTHER PUBLICATIONS

European Search Report dated Jun. 18, 2019 from European Application No. 19150203.8.
(Continued)

*Primary Examiner* — Marcela I. Shirsat

(57) ABSTRACT

A adaptor is used with a driver, a drill, and a cannula to facilitate removal of material from bone and placement of the cannula in the bone. The adaptor includes an end portion provided at a proximal first end that is configured to engage a portion of the drill; a body portion attached to the end portion and extending from the end portion toward a distal second end; a head portion provided at the distal second end and attached to the body portion; and a passageway for receiving the drill that extends through the adaptor. Furthermore, the head portion includes a distal surface and at least one coupler provided on or adjacent the distal surface for releasably engaging, the cannula.

20 Claims, 7 Drawing Sheets

(51) Int. Cl.
*A61B 17/17* (2006.01)
*A61M 5/158* (2006.01)
*A61B 10/02* (2006.01)
*A61B 17/34* (2006.01)
*A61B 17/00* (2006.01)
*A61B 90/00* (2016.01)

(52) U.S. Cl.
CPC ...... *A61B 17/1628* (2013.01); *A61B 17/1633* (2013.01); *A61B 10/025* (2013.01); *A61B 17/162* (2013.01); *A61B 17/1624* (2013.01); *A61B 17/1671* (2013.01); *A61B 17/1757* (2013.01); *A61B 17/3472* (2013.01); *A61B 17/8819* (2013.01); *A61B 2017/0046* (2013.01); *A61B 2017/00477* (2013.01); *A61B 2090/062* (2016.02); *A61M 5/158* (2013.01); *A61M 2005/1585* (2013.01)

(58) Field of Classification Search
USPC .................................................. 606/180, 171
See application file for complete search history.

(56) References Cited

U.S. PATENT DOCUMENTS

| | | | |
|---|---|---|---|
| 5,113,571 A | 5/1992 | Manska | |
| 5,120,312 A * | 6/1992 | Wigness | A61M 37/00 604/175 |
| 5,449,370 A * | 9/1995 | Vaitekunas | A61B 17/3476 606/169 |
| 5,575,794 A | 11/1996 | Walus et al. | |
| 6,575,919 B1 * | 6/2003 | Reiley | A61B 17/34 600/567 |
| 7,699,850 B2 | 4/2010 | Miller | |
| 7,850,620 B2 | 12/2010 | Miller et al. | |
| 8,414,585 B2 | 4/2013 | Meneghini et al. | |
| 8,944,069 B2 | 2/2015 | Miller et al. | |
| 8,998,848 B2 | 4/2015 | Miller et al. | |
| 9,192,759 B2 | 11/2015 | Hamilton | |
| 9,339,294 B2 | 5/2016 | Mandeen et al. | |
| 9,433,400 B2 | 9/2016 | Miller | |
| 9,504,477 B2 * | 11/2016 | Miller | B23B 45/00 |
| 9,510,910 B2 | 12/2016 | Miller et al. | |
| 9,687,255 B2 | 6/2017 | Sennett et al. | |
| 9,717,564 B2 | 8/2017 | Miller et al. | |
| 9,757,135 B1 | 9/2017 | Kelley | |
| 9,839,425 B2 | 12/2017 | Zergiebel et al. | |
| 9,844,362 B2 | 12/2017 | McWeeney | |
| 9,883,853 B2 | 2/2018 | Woodard et al. | |
| 10,004,504 B2 | 6/2018 | Bryant | |
| 2004/0215102 A1 | 10/2004 | Ikehara et al. | |
| 2010/0145142 A1 | 6/2010 | Begemann et al. | |
| 2011/0245833 A1 | 10/2011 | Anderson | |
| 2012/0053588 A1 | 3/2012 | Lozier et al. | |
| 2012/0232658 A1 | 9/2012 | Morgenstern Lopez et al. | |
| 2013/0041345 A1 | 2/2013 | Kilcoin et al. | |
| 2015/0230823 A1 | 8/2015 | Morgan et al. | |
| 2016/0022282 A1 | 1/2016 | Miller et al. | |
| 2016/0120553 A1 | 5/2016 | Xie | |
| 2016/0228131 A1 | 8/2016 | Brockman et al. | |
| 2017/0049460 A1 | 2/2017 | Coope | |

FOREIGN PATENT DOCUMENTS

| | | |
|---|---|---|
| EP | 1374784 B1 | 1/2001 |
| EP | 3517059 | 7/2019 |
| FR | 2344267 A1 | 10/1977 |
| WO | 99/12481 | 3/1999 |
| WO | 2008/0011262 | 1/2008 |
| WO | 2013179013 A1 | 12/2013 |
| WO | 2015/0006296 | 1/2015 |
| WO | WO 2017/074507 | 5/2017 |

OTHER PUBLICATIONS

Office Action dated May 4, 2020 from corresponding European Application No. 19150203.8.
International Search Report and Written Opinion dated Apr. 6, 2020 for International Application No. PCT/US2020/013630.
Marcus Holmberg, PhD, Minimally Invasive Ponto Surgery—A New Perspective on Bone Anchored Surgery,Bone Conduction & Middle Ear, AudiologyOnline, Jul. 1, 2017. 10 pages.

* cited by examiner

ADAPTOR FOR USE WITH A DRIVER, A DRILL, AND A CANNULA FOR DRILLING INTO BONE

BACKGROUND OF THE INVENTION

Field of the Invention

The present invention is generally directed to an adaptor used to aid in the placement of a cannula into bone. More particularly, the present invention is directed to an adaptor for releasably coupling to a cannula and engagement to a driver to facilitate manipulation of the cannula using the driver. More specifically, the present invention is directed to an adaptor for affording forward linear force applied to a driver to be transferred through the adaptor to a cannula releasably coupled to the adaptor, and for preventing a drill from extending more than a desired amount out of the cannula in order to facilitate placement of the cannula into bone.

Description of the Prior Art

Cannulas are used to afford access to portions of the human body. Such cannulas provide access to a portion of the human body via a passageway extending therethrough. Typically, a cannula is manipulated by a user, such as a surgeon, to facilitate placement in the human body. If the cannula is to provide access to bone, the surgeon can manipulate the cannula by hand to a position adjacent the bone, and then apply blunt force to the cannula to facilitate its placement into the bone. A drill can then be inserted through the passageway in the cannula to remove material from the bone. In doing so, an aperture is formed in the bone. Thereafter, instruments can be inserted through the passageway in the cannula to the aperture formed in the bone. As such, the process for placing cannulas has typically required multiple steps, and these multiple steps add complexity to surgeries involving the placement of such cannulas into bone. Therefore, there is a need for tools that simplify placement of cannulas into bone. Such tools can include an adaptor that affords forward linear force applied to a driver to be transferred through the adaptor to a cannula releasably coupled to the adaptor, and prevents a drill from extending more than a desired amount out of the cannula in order to facilitate placement of the cannula into bone.

SUMMARY OF THE INVENTION

The present invention in one preferred embodiment contemplates an adaptor for use with a driver, a drill, and a cannula, the adaptor including a proximal first end, an opposite distal second end, a mid-longitudinal axis extending through the proximal first end and the distal second end, a length extending between the proximal first end and the opposite distal second end, an end portion provided at the proximal first end, the end portion being configured to engage a portion of the drill, a body portion attached to the end portion and extending from the end portion toward the distal second end, a head portion provided at the distal second end, the head portion being attached to the body portion, the head portion including a distal surface and at least one coupler provided on or adjacent the distal surface, the at least one coupler being configured to releasably engage the cannula, and a passageway extending through the end portion, the body portion, and the head portion, the passageway extending between a first opening formed in the end portion and a second opening formed in the head portion, the mid-longitudinal axis extending through the passageway, the passageway being configured to receive a portion of the drill therethrough.

The present invention in another preferred embodiment contemplates an assembly for removal of material from bone and placement of at least a portion of the assembly in the bone, the assembly including an adaptor having a proximal first end, an opposite distal second end, a mid-longitudinal axis extending through the proximal first end and the distal second end, a length extending between the proximal first end and the opposite distal second end, an end portion provided at the proximal first end, the end portion being configured to engage a portion of a drill, a body portion attached to the end portion and extending from the end portion toward the distal second end, a head portion provided at the distal second end, the head portion being attached to the body portion, the head portion including a distal surface and at least one coupler provided on or adjacent the distal surface, the at least one coupler being configured to releasably engage a cannula, and a passageway extending through the end portion, the body portion, and the head portion, the passageway extending between a first opening formed in the end portion and a second opening formed in the head portion, the mid-longitudinal axis extending through the passageway, the passageway being configured to receive a portion of the drill therethrough; a driver having a chuck configured to engage a portion of the drill, the driver being configured to rotate the drill engaged to the chuck in at least one rotational direction; a drill including a key portion for engaging the chuck of the driver, a collar portion for engaging the end portion of the adaptor, and a shaft portion including flutes facilitating removal of material from the bone; and a cannula having at least one complementary coupler for engaging the at least one coupler on the adaptor, the engagement of the at least one coupler and the at least one complementary coupler preventing rotation of the adaptor and the cannula with respect to one another in at least one rotational direction.

The present invention in yet another preferred embodiment contemplates an assembly for removal of material from bone and placement of at least a portion of the assembly in the bone, the assembly including an adaptor having a proximal first end, an opposite distal second end, a mid-longitudinal axis extending through the proximal first end and the distal second end, a length extending between the proximal first end and the opposite distal second end, an end portion provided at the proximal first end, the end portion being configured to engage a portion of a drill, a body portion attached to the end portion and extending from the end portion toward the distal second end, a head portion provided at the distal second end, the head portion being attached to the body portion, the head portion including a distal surface and at least one coupler provided on or adjacent the distal surface, and a passageway extending through the end portion, the body portion, and the head portion, the passageway extending between a first opening formed in the end portion and a second opening formed in the head portion, the mid-longitudinal axis extending through the passageway, the passageway being configured to receive a portion of the drill therethrough; a driver having a chuck configured to engage a portion of the drill, the driver being configured to rotate the drill engaged to the chuck in at least one rotational direction; and a drill including a key portion for engaging the chuck of the driver, a collar portion for engaging the end portion of the adaptor, and a shaft portion including flutes facilitating removal of material from the bone.

These and other objects of the present invention will be apparent from review of the following specification and the accompanying drawings.

DETAILED DESCRIPTION OF THE PREFERRED EMBODIMENT

Figure 1:
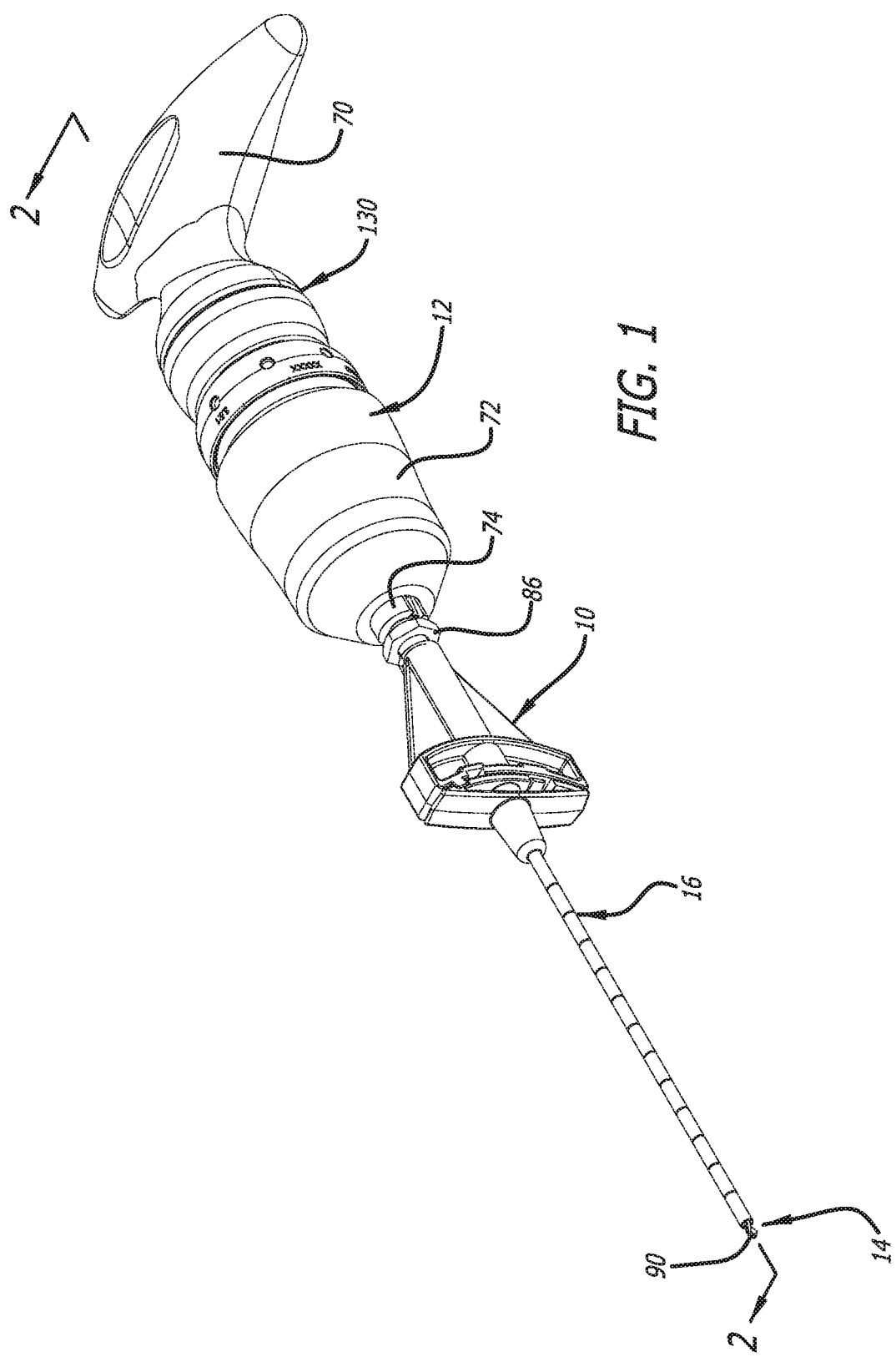
FIG. 1 is perspective view of an adaptor or spacer assembled with a cannula attached to the adaptor, a drill extending through the adaptor and the cannula, and a driver attached to the drill.
Figure 2:
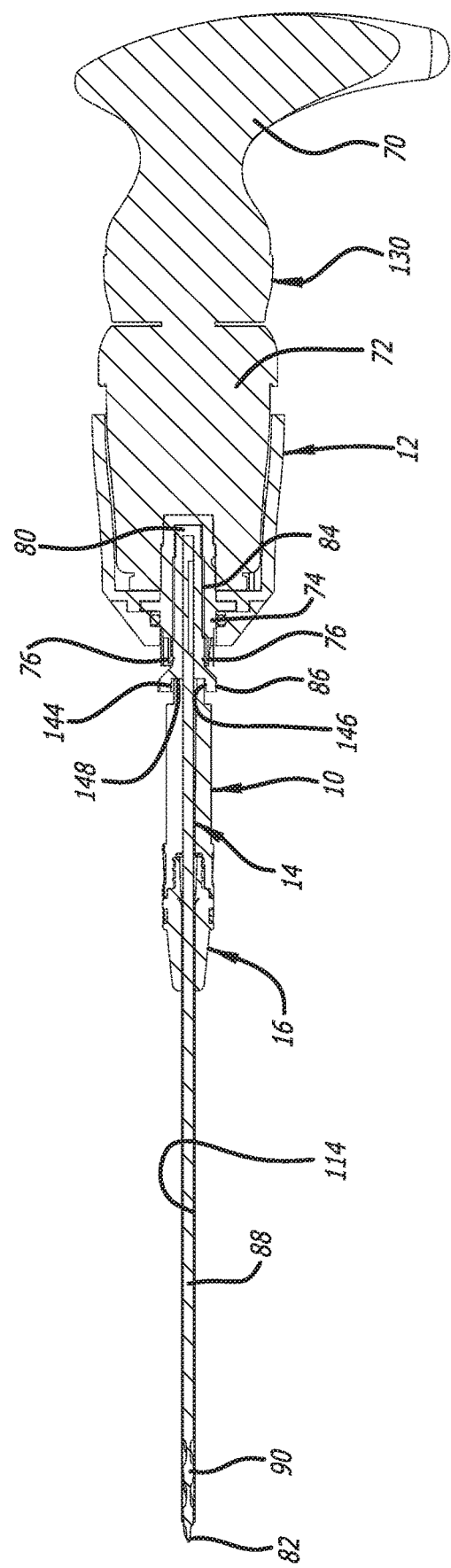
FIG. 2 is a cross-section of the assembly along Line 2-2 of FIG. 1.
Figure 3:
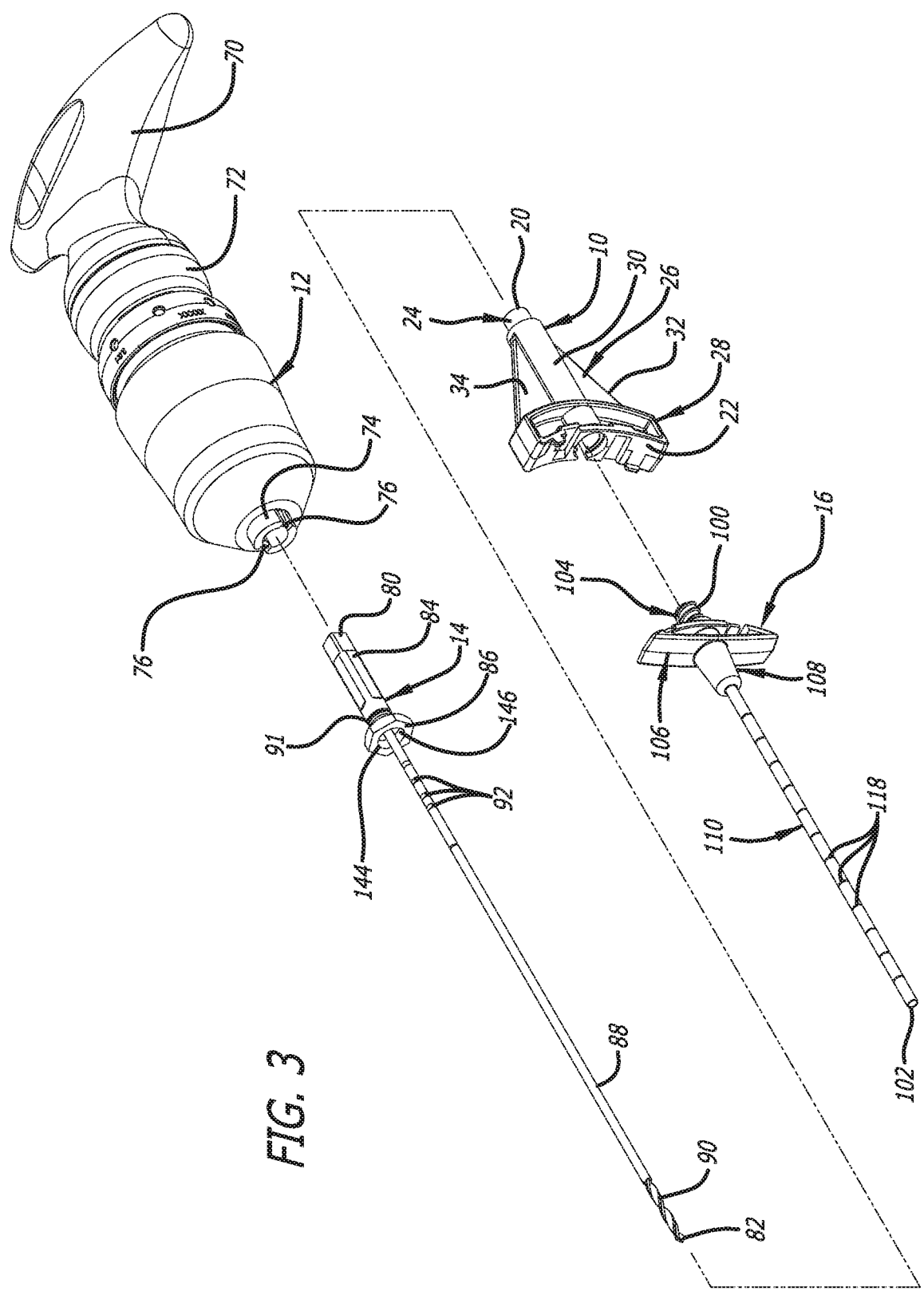
FIG. 3 is an exploded perspective view of the assembly of FIG. 1.

An adaptor or spacer according to one embodiment of the present invention is generally indicated by the numeral 10 in FIGS. 1-6. As depicted in FIGS. 1-3, the adaptor 10 is used in conjunction with a driver 12, a drill 14, and a cannula 16. The adaptor 10 can be used to afford placement of the drill 14 and the cannula 16 into bone such as a vertebral body. For example, the use of the drill 14 and the cannula 16, as discussed below, can afford access to the interior of the vertebral body.

When the adaptor 10, the driver 12, the drill 14, and the cannula 16 are assembled, the adaptor 10 can serve to afford forward linear force applied to the driver 12 to be transferred through the adaptor 10 to the cannula 16, and to prevent the drill 14 from extending more than a desired amount out of the cannula 16. Additionally, the adaptor 10 can also serve to impart rotational movement of the drill 14 to the cannula 16. As such, the adaptor 10 aids placement of the cannula 16 into bone.

As depicted in FIGS. 1-6, the adaptor 10 includes a proximal end 20 and a distal end 22 opposite from one another, and a mid-longitudinal axis extending the proximal end 20 and the distal end 22. The adaptor 10 includes a end portion 24, a body portion 26, and a head portion 28.

The end portion 24 is provided at the proximal end 20, the body portion 26 extends from the end portion 24 to the head portion 28, and the head portion 28 is provided at the distal end 22. As depicted in FIGS. 1-6, the end portion 24 is cylindrical, and the body portion 26 includes a middle portion 30 and first and second reinforcing struts 32 and 34 on opposite sides of the middle portion 30. Furthermore, as depicted in FIGS. 1-6, the head portion 28 includes a proximal surface 36 and a distal surface 38 opposite from one another, a first side surface 40 and a second side surface 42 opposite from one another, a first internal web portion 44, a second internal web portion 46, and a middle portion 48.

Figure 4:
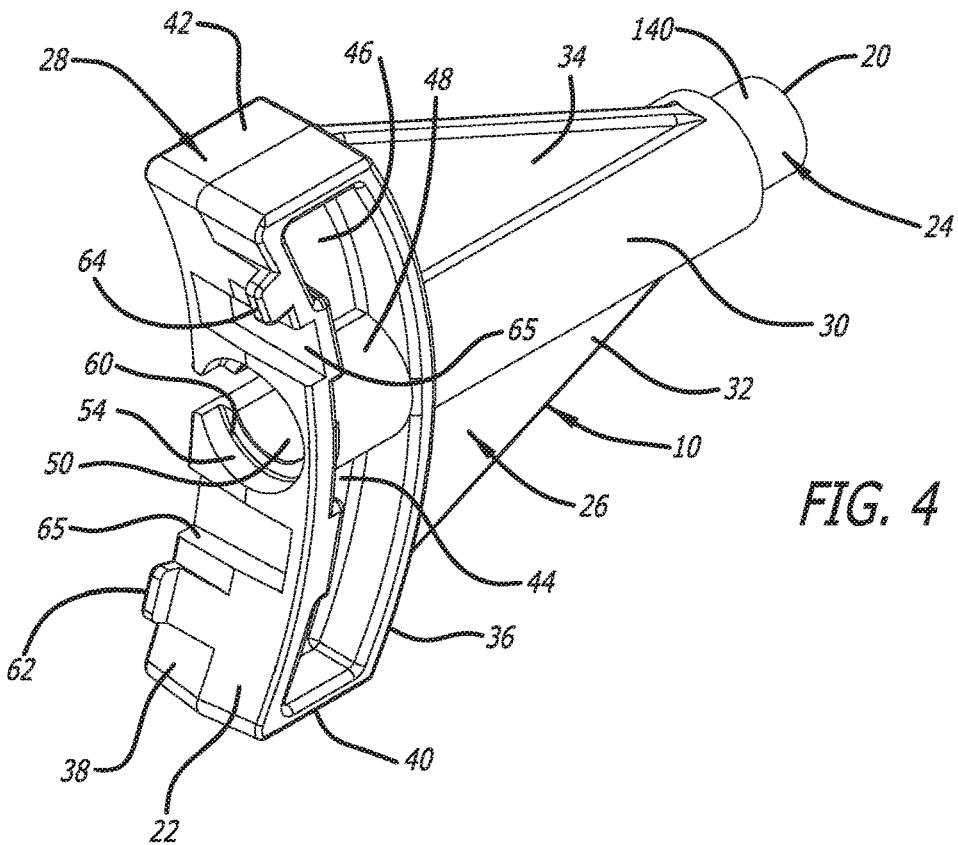
FIG. 4 is a first enlarged perspective view of the adaptor from a first side thereof at a distal end thereof.
Figure 5:
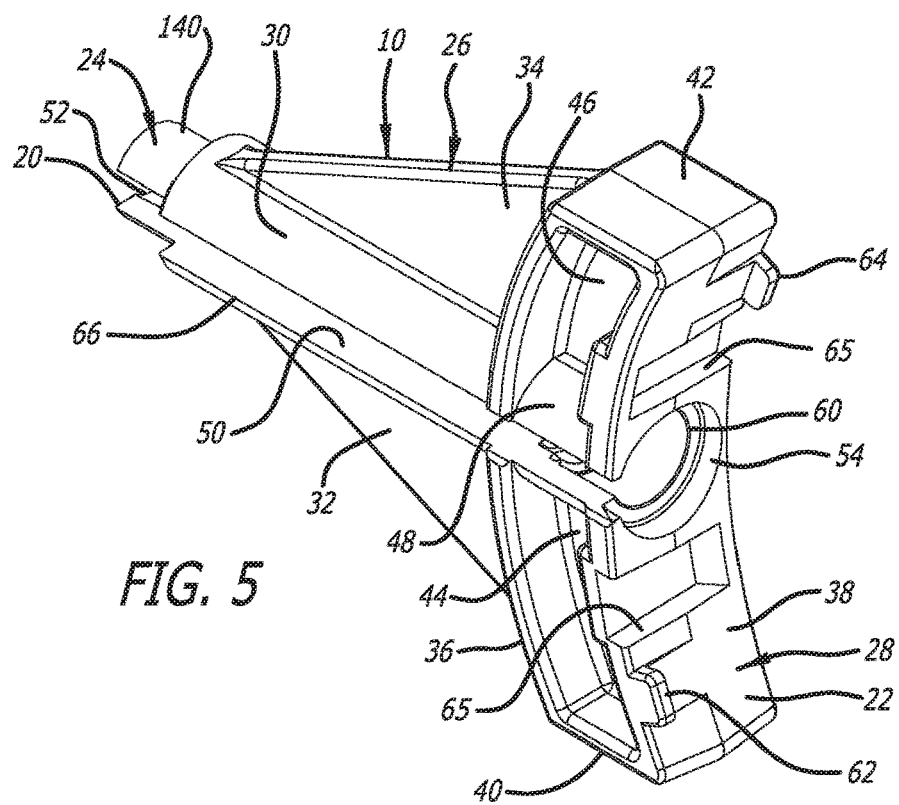
FIG. 5 is a second enlarged perspective view of the adaptor from a second side thereof at the distal end thereof.
Figure 6:
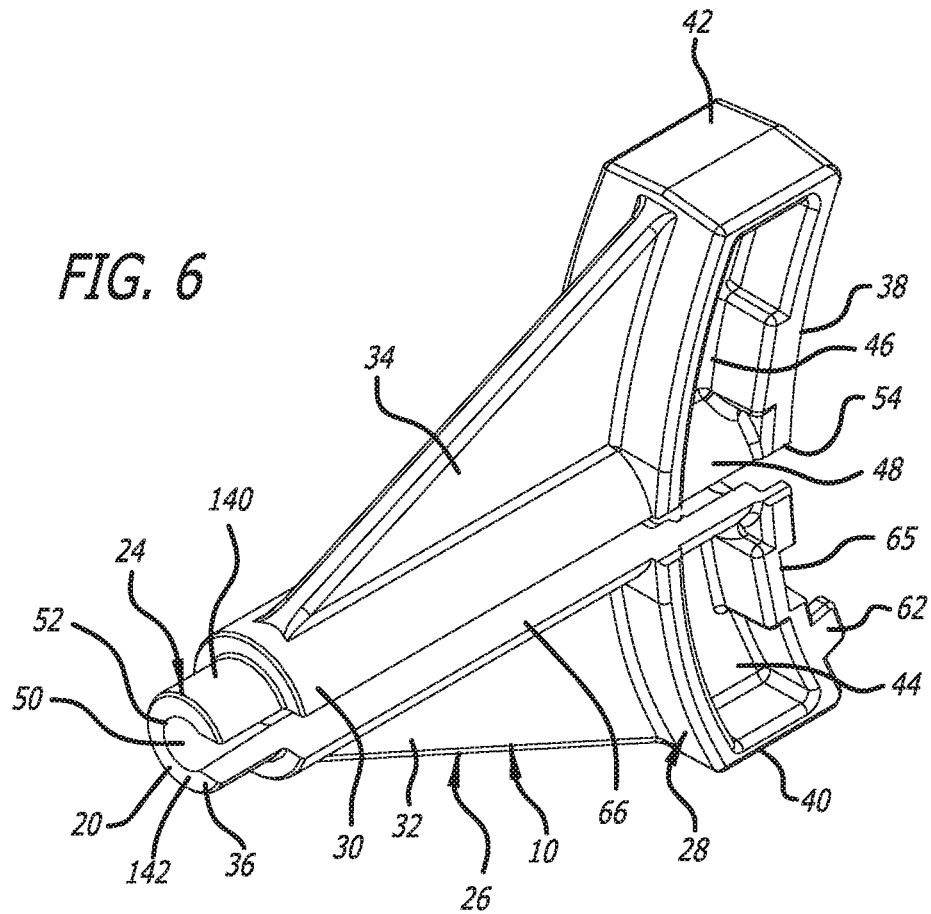
FIG. 6 is a third enlarged perspective view of the adaptor from the second side thereof at a proximal end thereof.

As depicted in FIGS. 4-6, the adaptor 10 includes a passageway 50 for receiving a portion of the drill 14 extending therethrough. The passageway 50 extends through the end portion 24, the middle portion 30 of the body portion 26, and the middle portion 48 of the head portion 28. The passageway 50 extends from a first opening 52 formed in the end portion 24 at the proximal end 20 of the adaptor 10 to a second opening 54 formed in the distal surface 38 of the head portion 28 at the distal end 22 of the adaptor 10. The passageway 50 is configured to receive a portion of the drill 14 therethrough, and the passageway 50 is configured to receive a portion of the cannula 16 at the distal end 22.

The adaptor 10, as depicted in FIGS. 1-3, is configured for releasably coupling to the cannula 16. To that end, the adaptor 10 includes at least one coupler. For example, the passageway 50 adjacent the second opening 54 can include a coupler such as threads 60, and the distal surface 38 can include a coupler such as a first tab 62, a second tab 64, and recesses 65. The threads 60, the first tab 62, the second tab 64, and one of the recesses 65 can facilitate releasable coupling with the cannula 16. Such engagement can prevent movement of the adaptor 10 and the cannula 16 with respect to one another.

Furthermore, a channel 66 can extend between the proximal end 20 and the distal end 22 of the adaptor 10. The channel 66 provides access to the passageway 50 extending through the adaptor 10.

As depicted in FIGS. 1-3, the driver 12 includes a handle portion 70, a body portion 72, and a chuck 74. The chuck 74 includes detents 76 for facilitating engagement with the drill 14. Furthermore, the handle portion 70 is rotatable relative to the body portion 72, and rotation of the handle portion 70 by a user causes corresponding rotation of the chuck 74. As such, the user can manipulate the handle portion 70 to force the driver 12 forward linearly, and to cause rotation of the chuck 74. As discussed below, such forward linear force and rotation of the chuck 74 is used to facilitate insertion of the drill 14 and the cannula 16 into the vertebral body.

The drill 14, as depicted in FIGS. 1-3, includes a proximal end 80 and a distal end 82 opposite from one another. The drill 14 includes a key portion 84 at the proximal end 80, a collar portion 86 provided adjacent the key portion 84, a shaft portion 88 extending from the key portion 84 through the collar portion 86 toward the distal end 82. The shaft portion 88 includes a tip portion 90 at the distal end 82 including flutes facilitating removal of material from the bone. The key portion 84 can be received in and engaged to the chuck portion 74 of the driver 12, The key portion 84 can include a recess 91 for receiving the detents 76 of the chuck 74. Furthermore, the chuck portion 74 and the key portion 84 can be magnetized to secure the engagement therebetween. As such, rotation of the chuck portion 74 via manipulation of the handle portion 70 also rotates the drill 14.

The shaft portion 88 also includes various exterior markings 92 adjacent the collar portion 86. During use of the drill 14, as discussed below, the exterior markings 92 allow the user to determine the depth of the tip portion 90 in the bone.

As depicted in FIGS. 1-3 and 7, the cannula 16 includes a proximal end 100 and a distal end 102 opposite from one another. The cannula 16 includes a post portion 104 at the proximal end 100, a handle portion 106 adjacent the post portion 104, a pedestal portion 108 adjacent the handle portion 106, and a shaft portion 110 extending from portions of the handle portion 106 and the pedestal portion 108 to the distal end 102.

The post portion 104, the handle portion 106, and the pedestal portion 108 can be unitarily formed with one another, and the shaft portion 110 can be secured within a passageway 112 extending through the post portion 104, the handle portion 106, and the pedestal portion 108. The shaft portion 110 includes a passageway 114 therethrough. The passageway 114, together with the portion of the passageway 112 in which the shaft portion 110 is not received, form a passageway 116 extending from the proximal end 100 to the distal end 102. The passageway 116 is configured to receive the shaft portion 88 of the drill 14 therethrough.

The shaft portion 110 also includes various exterior markings 118 therealong. During use of the cannula 16, as discussed below, the exterior markings 118 allow the user to determine the depth of the shaft portion 110 in the bone.

Figure 7:
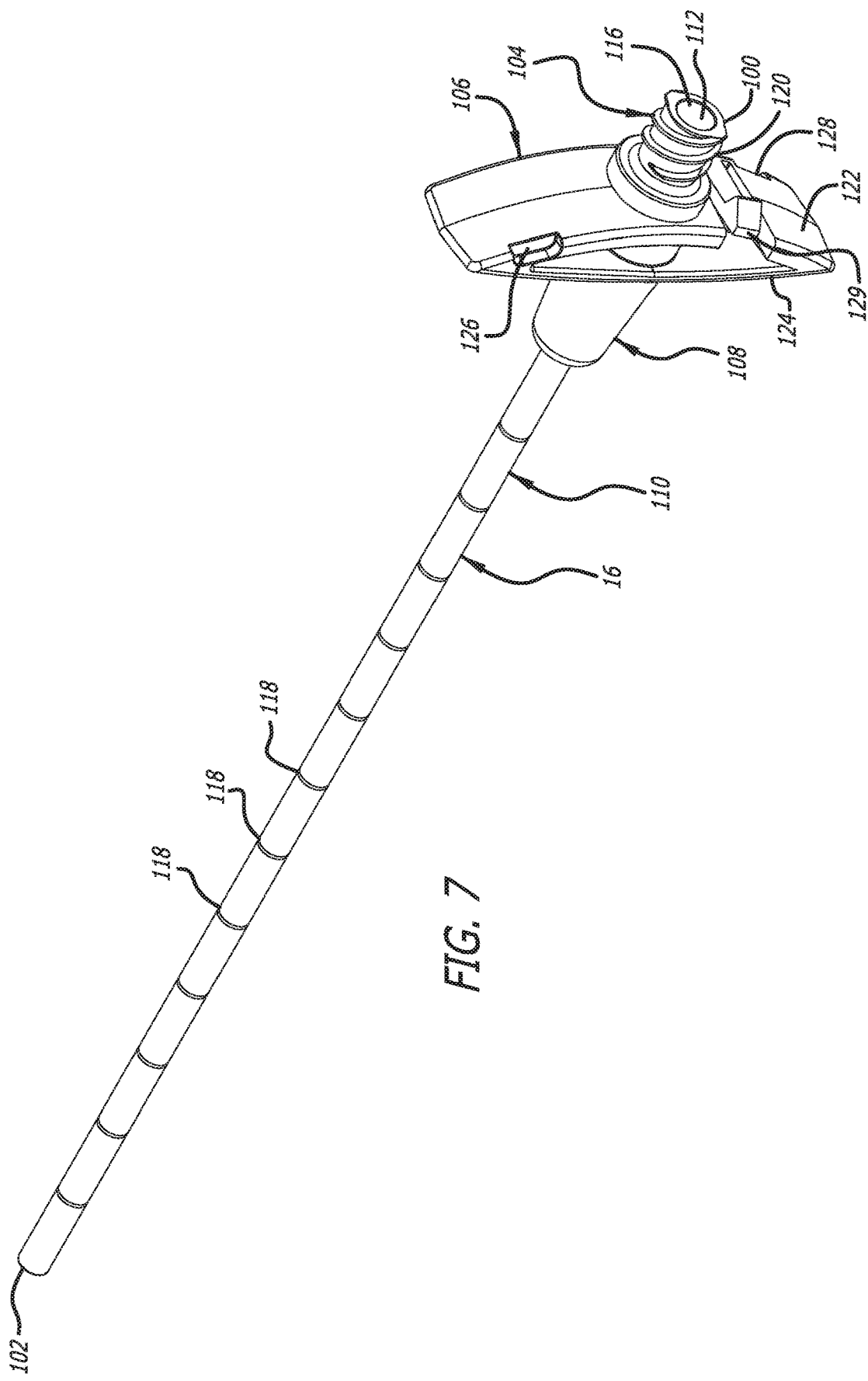
FIG. 7 is a first enlarged perspective view of a head portion of the cannula from a first side thereof at a proximal end thereof.
Figure 8:
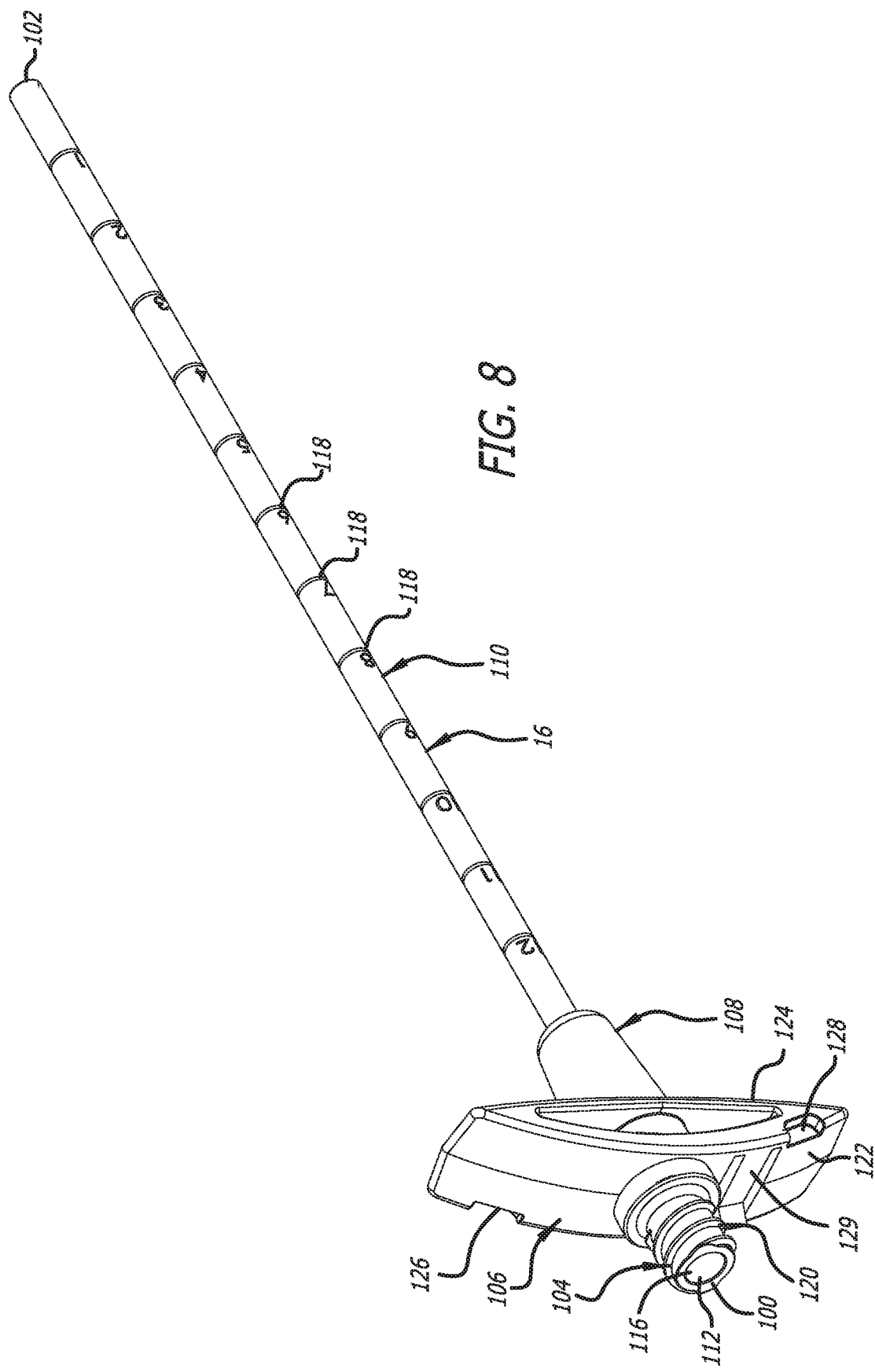
FIG. 8 is a second enlarged perspective view of the head portion of the cannula from a second side thereof at the proximal end thereof.

As depicted in FIG. 7, the post portion 104 includes threads 120 configured to engage the threads 60 in the passageway 50. Furthermore, the handle portion 106 includes a proximal surface 122 and a distal surface 124 opposite from one another. The proximal surface 122 includes a first recess 126, a second recess 128, and a detent 129 formed thereon. The first recess 126 is configured to receive and engage the first tab 62, the second recess 128 is configured to receive and engage the second tab 64, and the detent 129 is configured for receipt in one of the recesses 65.

When the threads 60 and 120 are engaged with one another, and the adaptor 10 and the cannula 16 are rotated with respect to one another to complete engagement of the threads 60 and 120, the first recess 126 comes into engagement with the first tab 62, the second recess 128 comes into engagement with the second tab 64, and the detent 129 comes into engagement with one of the recesses 65. Using the engagement of the threads 60 and 120 with one another, the engagement of the first tab 62 in the first recess 126, the engagement of the second tab 64 in the second recess 128, and the engagement of the detent 129 in one of the recesses 65, the adaptor 10 is releasably coupled to the handle portion 106 of the cannula 16.

To facilitate insertion of the cannula 16 into bone, the adaptor 10, the driver 12, the drill 14, and the cannula 16 can be assembled to one another as an assembly 130. Thereafter, the user can manipulate the assembly 130 to insert the shaft portion 110 of the cannula 16 into the bone. The adaptor 10 can be engaged to the handle portion 106 of the cannula 16 to prevent movement of the adaptor 10 and the cannula 16 with respect to one another. Furthermore, the drill 14 can be engaged to the driver 12 by inserting the key portion 84 into the chuck portion 74. The magnetic connection between the chuck portion 74 and the key portion 84, and engagement between the detents 76 and the recess 91 serve to secure the driver 12 and the drill 14 to one another.

Thereafter, the user can manipulate the driver 12 and the drill 14 to insert the shaft portion 88 of the drill 14 into the passageway 50 through the adaptor 10 and the passageway 116 through the cannula 16. After receipt therein, the shaft portion 88 of the drill 14 can be used to reinforce the shaft portion 110 of the cannula 16, Furthermore, the lengths of the shaft portion 88 of the drill 14 and the shaft portion 110 of the cannula 16 can be selected to adjust the amount that the tip portion 90 extends out of the shaft portion 110 at the distal end 102 of the cannula 16. The adaptor 10 can also be sized to prevent over-insertion of the tip portion 90 into the bone.

When the shaft portion 88 has been fully inserted into the adaptor 10 and the cannula 16, the end portion 24 of the adaptor 10 is received at least partially within and engages the collar portion 86 of the drill 14. As depicted in FIGS. 4-6, the end portion 24 includes an exterior surface 140 and an end surface 142. Furthermore, the collar portion 86 includes a recess 144, and as depicted in FIG. 2, the recess 144 includes an interior surface 146 and an end surface 148. The end surface 142 and the end surface 148 can be engaged with one another, and the exterior surface 140 and the interior surface 146 can be cylindrical to allow the drill 14 to rotate relative to the adaptor 10 without interference.

Forward linear force applied to the driver 12 is transferred to the drill 14, and engagement of the end surface 142 and the end surface 148 with one another also affords such forward linear force applied to the driver 12 to be transferred through the adaptor 10 to the cannula 16. That is, using the adaptor 10, the user can push on the driver 12 and such pushing force can ultimately be transferred to both the drill 14 and the cannula 16. Furthermore, the exterior surface 140 and the interior surface 146 are sized to allow the drill 14 to rotate relative to the adaptor 10 without interference. However, the friction due to contact between the end surface 142 and the end surface 148 can cause the adaptor 10 (and the cannula 16 attached thereto) to rotate with the drill 14. During use of the assembly 130, simultaneous rotation of the cannula 16 with the drill 14 during linear advancement can aid the penetration of the shaft portion 110 of the cannula 16 into the bone.

When using the assembly 130, the tip portion 90 is first contacted to the bone. Rotation of the drill 14 via use of the driver 12 causes the tip portion 90 to penetrate the bone. In doing so, the tip portion 90 forms an aperture in the bone. Furthermore, linear force applied to the driver 12 is transferred to the drill 14 and the cannula 16. Such linear force can aid penetration of the tip portion 90 and the shaft portion 110 of the cannula 16 into the bone. Furthermore, rotation of the cannula 16 with the drill 14 can aid penetration of the shaft portion 110 into the bone. The exterior markings 118 on the shaft portion 110 can be used to afford insertion of the shaft portion 110 to a proper depth in the bone.

After the cannula 16 has been positioned in the bone. The drill 14 can be removed from the passageway 50 and the passageway 116, and the adaptor 10 can be disconnected from the cannula 16. Thereafter, the drill 14 or another instrument can be reinserted into the passageway 116, The drill 14 can be used to further enlarge the aperture formed in the bone. If using the drill 14 without the adaptor 10, the markings 92 on the shaft portion 88 of the drill 14 can be used to afford insertion of the shaft portion 88 to a proper depth in the bone.

Once an aperture having a desired depth has been formed in the bone, another instrument (such as an ablation probe) can be inserted into the passageway 116 and into the aperture formed in the bone.

Alternatively, the handle portion 106 of the cannula 16 can be manipulated by the user to facilitate insertion thereof into the bone. The user can manipulate the handle portion 106 to insert the shaft portion 110 into the bone, and the exterior markings 118 on the shaft portion 110 can be used to afford insertion of the shaft portion 110 to a proper depth in the bone. The adaptor 10 can then be engaged to the handle portion 106 of the cannula 16 to prevent movement of the adaptor 10 and the cannula 16 with respect to one another. Thereafter, the shaft portion 88 of the drill 14 can be inserted through the passageway 50 and the passageway 116. The drill 14 can be attached to or detached from the driver 12 during initial insertion thereof into the passageway 50 and the passageway 116. The driver 12 can then be used to rotate the drill 14 to cause the tip portion 90 to penetrate the bone. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. An adaptor for use with a driver, a drill, and a cannula, the adaptor comprising:
    a proximal first end, an opposite distal second end, a mid-longitudinal axis extending through the proximal first end and the distal second end, a length extending between the proximal first end and the opposite distal second end,
    an end portion provided at the proximal first end, the end portion being configured to engage a portion of the drill,
    a body portion attached to the end portion and extending from the end portion toward the distal second end,
    a head portion provided at the distal second end, the head portion being attached to the body portion, the head portion including a distal surface, a first side and an opposite second side, and a third side and an opposite fourth side, the first side and the second side of the head portion being spaced apart across at least the distal surface, and the third side and the fourth side being spaced apart across at least the distal surface, the head portion including a first tab and a second tab extending outwardly from the distal surface, the first tab being positioned at or adjacent the first side of the head portion, the second tab being positioned at or adjacent the second side of the head portion, and the first tab and the second tab being configured to respectively engage complimentary structures formed on the cannula, and
    a passageway extending through the end portion, the body portion, and the head portion, the passageway extending between a first opening formed in the end portion and a second opening formed in the head portion, the mid-longitudinal axis extending through the passageway, the passageway being configured to receive a portion of the drill therethrough.

2. The adaptor of claim 1, further comprising at least one recess formed on the distal surface, the at least one recess being configured to engage a complimentary structure on the cannula.

3. The adaptor of claim 2, further comprising threads formed in the passageway adjacent the second opening, the threads being configured to engage complimentary threads on the cannula.

4. The combination of the adaptor of claim 3 with a cannula, the cannula comprising a first recess for receiving the first tab therein and a second recess for receiving the second tab therein, the engagement of the first tab with the first recess and the second tab with the second recess preventing rotation of the adaptor and the cannula with respect to one another in at least one rotational direction.

5. The combination of claim 4, wherein the cannula comprises the complimentary structure thereon for engaging the at least one recess, and the complimentary structure is a detent formed thereon, and the cannula comprises the complimentary threads thereon for engaging the threads formed in the passageway adjacent the second opening.

6. The adaptor of claim 1, further comprising a channel extending along a first side of the adaptor from the proximal first end to the distal second end, the channel communicating with and providing access to the passageway.

7. The combination of the adaptor of claim 1 with a drill, the drill comprising a collar portion including an annular recess having an annular interior surface and an end surface, wherein the end portion of the adaptor includes an annular exterior surface and an end surface, and when the end portion of the adaptor is engaged to the drill, the end portion is at least partially received in the annular recess, the end surface of the adaptor engages the end surface of the annular recess, and the end portion and the annular recess are independently rotatable with respect to one another.

8. The adapter of claim 1, wherein the first tab is positioned adjacent the third side, and the second tab is positioned adjacent the fourth side.

9. The adaptor of claim 8, wherein the first side and the second side are separated by a first distance in a first plane extending along the mid-longitudinal axis, and the third side and the fourth side are separated by a second distance in a second plane extending along the mid-longitudinal axis and perpendicular to the first plane, the first distance being less than the second distance.

10. An assembly for removal of material from bone and placement of at least a portion of the assembly in the bone, the assembly comprising:
    an adaptor having a proximal first end, an opposite distal second end, a mid-longitudinal axis extending through the proximal first end and the distal second end, a length extending between the proximal first end and the opposite distal second end, an end portion provided at the proximal first end and being configured to engage a portion of a drill, a body portion attached to the end portion and extending from the end portion toward the distal second end, a head portion provided at the distal second end, and a passageway extending through the end portion, the body portion, and the head portion, the head portion being attached to the body portion, the head portion including a distal surface, a first side and an opposite second side, and a third side and an opposite fourth side, the first side and the second side of the head portion being spaced apart across at least the distal surface, and the third side and the fourth side being spaced apart across at least the distal surface, the head portion including a first tab and a second tab extending outwardly from the distal surface, the first tab being positioned at or adjacent the first side of the head portion, and the second tab being positioned at or adjacent the second side of the head portion and the passageway extending between a first opening formed in the end portion and a second opening formed in the head portion, the mid-longitudinal axis extending through the passageway, the passageway being configured to receive a portion of the drill therethrough;
    a driver having a chuck configured to engage a portion of the drill, the driver being configured to rotate the drill engaged to the chuck in at least one rotational direction;
    a drill including a key portion for engaging the chuck of the driver, a collar portion for engaging the end portion of the adaptor, and a shaft portion including flutes facilitating removal of material from the bone; and
    a cannula having a first recess for receiving the first tab therein and a second recess for receiving the second tab therein, the engagement of the first tab with the recess and the second tab with the second recess preventing rotation of the adaptor and the cannula with respect to one another in at least one rotational direction.

11. The assembly of claim 10, further comprising at least one recess formed on the distal surface, the at least one recess being configured to engage a complimentary structure on the cannula.

12. The assembly of claim 11, further comprising threads formed in the passageway adjacent the second opening, the threads being configured to engage complimentary threads on the cannula.

13. The assembly of claim 12, wherein the complimentary structure of the cannula is a detent formed thereon for engaging the at least one recess formed on the distal surface.

14. The assembly of claim 10, further comprising a channel extending along a first side of the adaptor from the proximal first end to the distal second end, the channel communicating with and providing access to the passageway.

15. The assembly of claim 10, wherein the drill includes a collar portion including an annular recess having an annular interior surface and an end surface, the end portion of the adaptor includes an annular exterior surface and an end surface, and when the end portion of the adaptor is engaged to the drill, the end portion is at least partially received in the annular recess, the end surface of the adaptor engages the end surface of the annular recess, and the end portion and the annular recess are independently rotatable with respect to one another.

16. The assembly of claim 10, wherein the first tab is positioned adjacent the third side, and the second tab is positioned adjacent the fourth side.

17. An assembly for removal of material from bone and placement of at least a portion of the assembly in the bone, the assembly comprising:
an adaptor having a proximal first end, an opposite distal second end, a mid-longitudinal axis extending through the proximal first end and the distal second end, a length extending between the proximal first end and the opposite distal second end, an end portion provided at the proximal first end and being configured to engage a portion of a drill, a body portion attached to the end portion and extending from the end portion toward the distal second end, a head portion provided at the distal second end, and a passageway extending through the end portion, the body portion, and the head portion, the head portion being attached to the body portion, the head portion including a distal surface, a first side and an opposite second side, and a third side and an opposite fourth side, the first side and the second side of the head portion being spaced apart across at lease the distal surface, and the third side and the fourth side being spaced apart across at least the distal surface, the head portion including a first tab and a second tab extending outwardly from the distal surface, the first tab being positioned at or adjacent the first side of the head portion, the second tab being positioned at or adjacent the second side of the head portion, and the first tab and the second tab being configured to respectively engage complimentary structures formed on the cannula, and the passageway extending between a first opening formed in the end portion and a second opening formed in the head portion, the mid-longitudinal axis extending through the passageway, the passageway being configured to receive a portion of the drill therethrough;
a driver having a chuck configured to engage a portion of the drill, the driver being configured to rotate the drill engaged to the chuck in at least one rotational direction; and
a drill including a key portion for engaging the chuck of the driver, a collar portion for engaging the end portion of the adaptor, and a shaft portion including flutes facilitating removal of material from the bone.

18. The assembly of claim 17, wherein the drill includes a collar portion including an annular recess having an annular interior surface and an end surface, the end portion of the adaptor includes an annular exterior surface and an end surface, and when the end portion of the adaptor is engaged to the drill, the end portion is at least partially received in the annular recess, the end surface of the adaptor engages the end surface of the annular recess, and the end portion and the annular recess are independently rotatable with respect to one another.

19. The assembly of claim 18, further comprising a cannula, the cannula comprising a first recess for receiving the first tab therein and a second recess for receiving the second tab therein, the engagement of the first tab with the first recess and the second tab with the second recess.

20. The assembly of claim 17, wherein the first tab is positioned adjacent the third side, and the second tab is positioned adjacent the fourth side.

* * * * *